(12) United States Patent
Zhao

(10) Patent No.: US 11,219,648 B2
(45) Date of Patent: Jan. 11, 2022

(54) METHOD FOR PROCESSING TRADITIONAL CHINESE MEDICINE USING CALCIUM-BASED ION SOLUTION AND APPLICATION THEREOF

(71) Applicant: Jianguo Zhao, Shanghai (CN)

(72) Inventor: Jianguo Zhao, Shanghai (CN)

(73) Assignee: Jianguo Zhao, Shanghai (CN)

( * ) Notice: Subject to any disclaimer, the term of this patent is extended or adjusted under 35 U.S.C. 154(b) by 0 days.

(21) Appl. No.: 16/634,908

(22) PCT Filed: Aug. 4, 2017

(86) PCT No.: PCT/CN2017/096095
§ 371 (c)(1),
(2) Date: Jan. 29, 2020

(87) PCT Pub. No.: WO2019/024112
PCT Pub. Date: Feb. 7, 2019

(65) Prior Publication Data
US 2020/0316137 A1    Oct. 8, 2020

(51) Int. Cl.
*A61K 33/06* (2006.01)
*A61K 35/618* (2015.01)
*A61K 9/00* (2006.01)

(52) U.S. Cl.
CPC ............ *A61K 35/618* (2013.01); *A61K 33/06* (2013.01); *A61K 9/0014* (2013.01); *A61K 2236/39* (2013.01)

(58) Field of Classification Search
None
See application file for complete search history.

(56) References Cited

U.S. PATENT DOCUMENTS 6,458,361 B1 * 10/2002 Ng ............................ A61P 3/10
424/195.15

FOREIGN PATENT DOCUMENTS

| CN | 102028709 A | 4/2011 |
| CN | 104798891 A | 7/2015 |
| CN | 104873844 A | 9/2015 |
| CN | 105233010 A | 1/2016 |
| CN | 105327267 A | 2/2016 |
| CN | 103408604 B | 7/2016 |
| CN | 106266378 * | 1/2017 |
| CN | 106266378 A | 1/2017 |
| CN | 106727024 A | 5/2017 |
| CN | 107349227 A | 11/2017 |
| WO | 2016000508 A1 | 1/2016 |

OTHER PUBLICATIONS

Wang, Weihao Wang, Xiaotao, Wang, Zhiming, The Research of Liquor for Processing Traditional Chinese Medicine, China Journal of Chinee Material Medica, Feb. 28, 2006, p. 259-262, the 31st volume, the 3rd issue, Research Institute of China Academy of Chinese Medical Sciences, Beijing, China.

Takehiko Uematsu, Cellulose wet wiper sheets prepared with cationic polymer and carboxymethyl cellulose using a papermaking technique, Cellulose, Kluwer Academic Publishers(Dordrecht), Apr. 7, 2011 (Apr. 7, 2011), pp. 1129-1138, vol. 18, No. 4, XP019923257, ISSN:1572-882X, DOI:10.1007/S10570-011-9536-9, NL.

* cited by examiner

*Primary Examiner* — Ralph J Gitomer
(74) *Attorney, Agent, or Firm* — Mark M. Friedman

(57) ABSTRACT

A method for processing traditional Chinese medicine using a calcium-based ion solution and an application thereof. A solution formed by a calcium-based ion solution and Chinese spirits is used to soak a traditional Chinese medicine prescription; the calcium-based ion solution refers to a solution containing calcium ions with a mass percentage of 0.3-10%; and the Chinese spirits is a spirit containing more than 35% alcohol by volume. Also provided is an application of a soaking liquid for processing traditional Chinese medicine in preparing, from a traditional Chinese medicine prescription, a meridians and collaterals administration agent applied on skin, a preparation extracted from traditional Chinese medicine soaked using a soaking solution formed by "a calcium-based ion solution and a spirit" has a better effect of guiding skin penetration.

8 Claims, 1 Drawing Sheet

| Sample number | Sample name | Test items | Unit | Testing results | Testing basis |
|---|---|---|---|---|---|
| 2015100700 | Pearl extract (Z-20151014-102) | $Na^+$ | % | 0.01522 | Refer to JY/T 020-1996 |
| | | $Ca^{2+}$ | % | 2.45870 | |
| | | $Mg^{2+}$ | % | N.D. (<0.0001) | |
| | | $K^+$ | % | 0.00009 | |
| | | $Cl^-$ | % | 3.92 | |
| | | Br | % | N.D. (<0.001) | Refer to BS EN 14582-2007 |
| | | S | % | N.D. (<0.001) | |
| | | Moisture | % | 89.42 | Refer to GB/T 606-2003 |
| | | Protein | % | 0.044 | Refer to GB/T 5009.5-2010 |
| | | ICP-OES full scan | % | See Table 2-1 below | Refer to JY/T 015-1996 |
| Blank below | | | | | |

METHOD FOR PROCESSING TRADITIONAL CHINESE MEDICINE USING CALCIUM-BASED ION SOLUTION AND APPLICATION THEREOF

FIELD OF INVENTION

The invention belongs to the field of processing traditional Chinese medicine, and more specifically, relates to a method for processing traditional Chinese medicine using calcium-based ion solution and application thereof.

BACKGROUND OF INVENTION

In the *Inner Canon of Huangdi*, a Chinese medical masterpiece written 2,500 years ago, the meridians, as an important concept, runs through the book. It involves three ancient medical methods: moxibustion therapy, Bian-stone therapy (i.e., a medical treatment with stones) and guidance (an ancient breathing exercise), all of which are applied through the meridians. The *Inner Canon of Huangdi* also expounds the functions of the meridians: running breath and blood, balancing yin and yang, developing muscles, smoothing joints, connecting viscera with one's whole body, and transmitting pathogenic factors. During the Western Jin Dynasty (AD 265-317), *A-B Classic of Acupuncture and Moxibustion* written by Huang Fumi expounds the theory of viscera and meridians. During the Tang Dynasty (AD 581-682), *A Thousand Gold Pieces Prescriptions and Wings of the Thousand Gold Pieces Formulary* written by Sun Simiao expounds the synergy and application of meridians and acupoints. During the Qing Dynasty (AD 1742), *The Golden Mirror of Medicine* written by Wu Qian expounds the examples of meridian indications, and systematically discussed the relationship between viscera and meridians and their application.

The modern *TCM Internal Medicine* has such a comment on the meridians: Meridians are the channels through which breath and blood run in the human body, closely linking all the viscera, organs, opening orifices, skin and hair, muscles, bones and other tissues of the human body into a unified whole. Therefore, the meridians have a certain relationship in human physiological functions, pathological changes, symptoms, and diagnosis. The channels are the main body of the meridians, also known as the meridians. There are mainly twelve meridians, Ren meridian and Du meridian, these meridians are also known as the "acupoints of fourteen meridians". Each meridian has a specific connection with the viscera. These yin meridians and yang meridians are connected to each other to form an exterior-interior relationship. The "acupoints" are the points on the meridians, which are the intersection points of the channels and breath.

According to the theory of traditional Chinese medicine "Meridian Tropism", human viscera has the characteristic of selective absorption of drug flavor. It is of great significance in guiding clinical administration. After oral medicines enter the digestive tract, they take effect by being transported through the meridians to the corresponding viscera. Traditional Chinese medicine is oral-taken or skin-coated, which has been producing unsatisfactory results due to its penetrability and absorption rate.

The quality of traditional Chinese medicine processing directly affects the effect of medicine, thus, Chinese famous doctors attach great importance to the processing methods of traditional Chinese medicine. Zhang Zhongjing, a doctor of the Han Dynasty, divides the decoction water into rainwater, worked water, etc.; Xu Lingtai thinks that: "the decoction method needs great attention, whether the medicine is effective or not depends entirely on this"; Li Shizhen pointed out that the adverse consequences of improper decoction: "Although the decoction of high quality is prepared according to established methods, if the decoction is processed recklessly, the water and fire do not match each other, and the fire is out of order, the decoction will not be effective." All of these indicate that the ancients have realized that there are many factors affecting the quality of the decoction during the processing (decocting), and the quality of the processing directly affects the efficacy of traditional Chinese medicine.

There are two changes in the processing of traditional Chinese medicine: one is the dissolution of the active ingredients of the medicine; the other is the chemical reaction of various physiologically active ingredients in the medicine. Therefore, a lot of special attention should be paid to the processing method of the decoction.

Soaking is also an important part of processing traditional Chinese medicine. Soaking before decocting Chinese herbal pieces is not only beneficial to the full dissolution of active ingredients, but also can shorten the decocting time, so as to avoid excessive consumption and destruction of some active ingredients due to the excessive decocting time. Most medicines should be soaked in cold water. First, pour the medicine into the pot to spread it out, and then add normal temperature water-room temperature water to soak for 60 minutes, the water will be about 2 centimeters higher than the medicine plane when one presses the medicine gently. Take fully soaking of medicinal materials as a principle. In case of corruption and deterioration, the soaking time in summer should not be too long due to the high temperature, while the soaking time in winter could be longer. It is especially important to note that Chinese medicines must never be soaked in boiling water.

Amid traditional Chinese medicine processing, there is also a set of customary rules for selecting the soaking water, that is, the decocting or soaking water must be odorless, clean and clear, with less minerals and impurities. Generally speaking, drinkable water in daily life can be used to decoct traditional Chinese medicine. Generally, clear spring water, river water and tap water can be used, while well water with better water quality should be selected. Traditionally, it is best to use purified and softened drinking water to reduce impurities and prevent precipitation between calcium, magnesium plasma in water and medicine ingredients.

Influenced by this traditional concept, the soaking water is usually tap water or pure water with relatively simple composition, and almost no mineral-rich aqueous solution is selected.

SUMMARY OF INVENTION

The first purpose of the invention is to provide a method for processing traditional Chinese medicine using calcium-based ion solution.

The second purpose of the invention is to provide a transdermal administration route of traditional Chinese medicine prescription obtained by the method of processing traditional Chinese medicine with calcium-based ion solution. transdermal and meridians therapy.

The third purpose of the invention is to provide a soaking solution for processing traditional Chinese medicine in a higher penetrability and absorption rate.

The fourth purpose of present invention is to apply the soaking liquid for processing traditional Chinese medicine into making the transdermal administration coating agent of traditional Chinese medicine prescription.

In order to achieve the first purpose of the invention, the invention discloses the following technological scheme: a method for processing traditional Chinese medicine using calcium-based ion solution is characterized in that ingredients of the traditional Chinese medicine are soaked in a solution of a calcium-based ion solution and Chinese baijiu, and the calcium-based ion solution refers to a solution with a mass percentage concentration of calcium ion of 0.3%-10%, and the Chinese baijiu is at 35-75% alcohol by volume.

As a preferred scheme, the calcium-based ion solution is obtained by soaking shells in a dilute hydrochloric acid solution, and the shells refer one or more of oyster shell, clam shell, pearl, abalone shell, sea clam, clam, big clam, giant clam, purple shell, snail, siput, shrimp shell and crab shell.

As a preferred scheme, the traditional Chinese medicine is for treating freckles, eye bags, skin whitening, hair tonic, dandruff shampoo, gout, vitiligo, eczema, psoriasis, itchy skin, arthritis and degenerative diseases, foot dampness dispelling, athlete's foot, foot dredge meridians, female mammary hyperplasia, stretch marks, prostatitis, skin cancer, hyperglycemia, hyperlipidemia, prostatic hyperplasia, urinary tract infection, chronic nephritis, proteinuria, uterine fibroids, lung nodules, liver cysts, gallstones, fatty liver, neurasthenia, tumors, cervical spondylosis, pain of neck, shoulder, low-back and leg, muscle cramp, frozen shoulder, sports muscle injury, male sexual function, Parkinson's disease, cardiovascular diseases, trigeminal neuralgia, mastitis, neuropathic pain, Alzheimer's disease, eye disorders and for treating diseases related to wormwood extract.

In order to achieve the second purpose of the invention, the invention discloses the following technological scheme: the transdermal administration route of traditional Chinese medicine prescription obtained by the method of processing traditional Chinese medicine with calcium-based ion solution is a transdermal and meridians therapy.

In order to achieve the third purpose of the invention, the invention discloses the following technological scheme: a soaking solution for processing a traditional Chinese medicine is characterized in that the soaking solution is a solution composed of calcium-based ion solution and Chinese baijiu. The calcium-based ion solution refers to a solution with a mass percentage concentration of calcium ion of 0.3%-10%, and the Chinese baijiu is at 35-75% alcohol by volume.

As a preferred scheme, the calcium-based ion solution is obtained by soaking shells in a dilute hydrochloric acid solution, and the shells refer one or more of oyster shell, clam shell, pearl, abalone shell, sea clam, meretrix meretrix linnaeus, clam, big clam, tridacna, purple shell, snail, siput, shrimp shell and crab shell.

In order to achieve the fourth purpose of the invention, the invention discloses the following technological scheme: the soaking solution for processing traditional Chinese medicine is applied in making the transdermal administration coating agent of traditional Chinese medicine prescription.

As a preferred scheme, the traditional Chinese medicine is for treating hyperglycemia, hyperlipidemia, prostatic hyperplasia, urinary tract infection, chronic nephritis, proteinuria, uterine fibroids, lung nodules, liver cysts, gallstones, fatty liver, neurasthenia, tumors, cervical spondylosis, pain of neck, shoulder, low-back and leg, muscle cramp, frozen shoulder, sports muscle injury, male sexual function, Parkinson's disease, cardiovascular diseases, trigeminal neuralgia, mastitis, neuropathic pain, Alzheimer's disease, eye disorders and for treating diseases related to wormwood extract.

The advantage of the invention: the preparation which is extracted from the traditional Chinese medicine soaked in the solution composed of "calcium-based ion solution and the Chinese baijiu" has better effect of guiding skin penetration, puts forward a new administration route and solves the problem that traditional Chinese medicine prescriptions cannot be administered through skin, meridians and acupoints. With synergy of Calcium-based ion solution and the Chinese baijiu, the administration route of some oral-taking traditional Chinese medicine can be changed. Through external application, the irritation to intestine and stomach and the damage to liver and kidney caused by orally taking traditional Chinese medicine could be avoided, so as to treat internal diseases with external therapy.

1. Applying the preparation to skin externally can relieve or suppress neuropathic pain of the local peripheral nerve and treat neuropathic prickling and so on.

2. The preparation can be directly absorbed by skin to change the administration route of some oral-taking traditional Chinese medicine through the digestive tract, so that traditional Chinese medicine's irritation to the digestive tract and its side effect on liver and kidney and changes of gastrointestinal enzymes and intestinal flora to drug resistance can be avoided.

3. According to the theory of traditional Chinese medicine "Meridian Tropism", the preparation can be directly applied on skin, meridians and acupoints. By the transdermal administration route, the effective ingredients of the preparation can be absorbed by meridians to change the local environment of the corresponding viscera, repair or restore the function of the viscera. The purpose of treating the visceral disorder is achieved, and the administration is more direct and the effect is more obvious.

4. The method of extracting the preparation can greatly improve the use efficiency of the medicine. The actual test production process confirmed that the original one-day dose (a dose) can now be used for a course—15 days. It can improve the utilization rate of medicine resources, which is significant for the protection and rational utilization of traditional Chinese medicine.

BRIEF DESCRIPTION OF DRAWINGS

The FIGURE shows the test results of ion content obtained from the calcium-based ion solution by pearl extraction.

DETAILED DESCRIPTION

The invention is further illustrated combining with specific implements below. The experimental methods used in the following implements are conventional methods unless otherwise specified. The materials, reagents and the like used in the following implements are commercially available unless otherwise specified. It shall be understood that the implements are used only to illustrate the invention but not to limit its scope.

(I) Overview: The calcium-based ion solution used is an active organic hydrophilic ion solution extracted from shellfish, shrimp and crab shells, and the soaking container is a non-metal covered glass.

1. The calcium-based ion solution specifies the calcium content in the solution as the standard value for measuring the dilution concentration of ionic solution (the calcium content in raw solution is 20%). When the ratio of the Chinese baijiu to the calcium-based ionic solution is 0.92:1.364/ml, the calcium content is 20% (extreme value). When one part by weight of the calcium-based ion solution is mixed with three parts by weight of Chinese baijiu at 60% alcohol by volume, the content of ion calcium is 5%, and so on, the dilution concentration of ionic solution could be calculated proportionally. Unless otherwise specified, the Chinese baijiu used is a pure grain edible wine at more than 35% alcohol by volume fermented by sorghum and wheat. And the Chinese baijiu at 60% alcohol by volume is preferred.

2. The calcium-based ion solution is diluted to 0.3%-10% for use, the threshold of the ion calcium content varies according to different diseases and uses.

(II) Procedures and methods before soaking the traditional Chinese medicine:

A. Before soaking the Chinese herbal medicine, preprocessing is needed.

(1) Clean the traditional Chinese medicine with Chinese baijiu at 35-75% alcohol by volume before soaking, to remove dust and impurities.

(2) Some nuts need to be peeled, cored, and crushed; roots need to be cut into pieces; some insects' heads, feet, and wings need to be removed. The specific herbs shall be preprocessed according to the prescription: such as stir-frying with honey, processing with wine and processing with vinegar.

(3) Do not wash with water. When the Chinese herbal medicine absorbs water, the alcohol concentration will decrease, affecting the extraction efficiency of and the transdermal administration effect.

B. Dilute the calcium-based ionic solution to the required concentration with Chinese baijiu at 60% alcohol by volume, and then fully stir for soaking.

C. Choose different traditional Chinese medicine prescriptions according to the patients' symptoms (the nature and flavor of traditional Chinese medicine shall satisfy the meridians of viscera and conform to the clinical guidance of "Meridian Tropism"). Soak the Chinese herbal medicine in the calcium-based ionic solution of specific concentration until fully soaked, and then apply the extracted preparation to the corresponding acupoints (pat lightly or massage the acupoints to help absorption). Recommend twice a day, apply an appropriate quantity each time. Overuse can cause skin allergy reaction. It will return to normal within two or three days after discontinuation. For overuse for a long time, there will be calcification on the skin, which will return to normal within two weeks after discontinuation. The technology is mainly aimed at the treatment of various chronic diseases such as visceral inflammation, tumors and cardiovascular system, and neuropathic pain and diseases of neck, shoulder, waist and leg.

(III) Comparative test:

For example: prostatic hyperplasia care solution

1. A sample of 10 participants: divided into group A and group B. 5 participants in each group.

2. Sample preparation: divided into solution A and solution B: soaked in different soaking solutions, and other conditions are the same.

3. Solution A: a preparation obtained by soaking Chinese herbal medicine in a solution composed of calcium-based ionic solution and Chinese baijiu.

4. Solution B: a preparation obtained by soaking Chinese herbal medicine in a single liquor.

5. Apply solution A at Shimen acupoint of Ren meridian (two fingers below the navel) on Group A. Spray 6 times (about 1 ml), twice a day, 15 days for a course. The effect is obvious.

6. Apply solution B by spraying 6 times (about 1 ml) at Shimen acupoint of Ren meridian on Group B, twice a day, 15 days for a course. It is ineffective. After a week of discontinuation, apply solution A in the same way for a course and then the effect is obvious.

7. Test conclusion: The traditional Chinese medicine preparation soaked in "calcium-based ion solution and Chinese baijiu" can guide skin penetration.

8. Note: Taboo: it should be used with caution in patients with allergic constitution.

(IV) The skin penetration guidance and pharmacological effect of the solution composed of calcium-based ion solution and Chinese baijiu.

1. The calcium-based ion solution is composed of ions with $Ca^{2+}$ as the main element and $Na^+$, $Mg^{2+}$, $K^+$, $Cl^-$, Br, S, etc. Human cells have channels for $Ca^{2+}$, $Na^+$, $K^+$, $Cl^-$. When a certain threshold ion is accumulated outside the skin, it affects the ions in the cell membrane, accelerating ion exchange inside and outside the cell membrane and promoting the medicine penetration at the same time. For this reason, calcium-based ion has permeability to skin tissue.

2. Calcium-based ion solution retains its own nature and flavor in addition to its skin penetration guidance. Since it is an active hydrophilic ion extracted from shell, so it has the natural attributes of the shell. According to the *Compendium of Materia Medica*: oyster shell [Nature and flavor] salty, mild, slightly cold, non-toxic. [Indications] Resolve phlegm and soften hard masses, clear heat, remove dampness, treat diarrhea, scrotum agglomeration, and thyroid disease tuberculosis. It has been used as an effective medicine for softening and resolving hard mass in all prescriptions. (Different shells have different nature and flavor and different effects.)

3. Chinese baijiu: According to the *Grand Dictionary of Chinese Medicine*: Chinese baijiu can disperse cold stagnation, remove blood stasisi, stimulate the stomach, dredge the meridians and balance yin and yang. According to the Practical Dictionary of Medicinal Property: Chinese baijiu is an effective medicine in clearing blood vessels and improving efficacy. According to the Traditional Chinese Medicine, records: Chinese baijiu. Nature and flavor: bitter, sweet, pungent, hot, entering the twelve meridians, functions and blood circulation, efficacy improvement. Indications are pain of muscles and meridians and other symptoms.

(V) The method of obtaining the ion solution from a shell through a chemical reaction

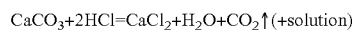

$$CaCO_3 + 2HCl = CaCl_2 + H_2O + CO_2\uparrow (+\text{solution})$$

Principle: Calcium carbonate reacts with hydrochloric acid to form calcium chloride, carbon dioxide and water, which are converted from solid calcium carbonate to liquid calcium chloride solution. (This solution contains the following components: $Na^+$, $Ca^{2+}$, $Mg^{2+}$, $K^+$, $Cl^-$, Br, S, and protein). A variety of ion solutions are naturally formed by the shell gene program, which we call "calcium-based ion solution."

Brief Description of the Proportion and Process Flow:

A. 1 Kg shell→wash, blow dry, crash to 3-5 mm block-→soak in 6000 ml dilute hydrochloric acid solution (hydrochloric acid solution concentration is below 3.5%)→rotate chemical reaction system→ion solution (primary product).

B. Primary product of sub-solution→negative filtration thrice→spray dry distillation→calcium ion concentration reaches 20% (raw solution)→stored for later use.

Note: The entire process is operated in non-metallic containers and non-metallic conduits.

The calcium-based ion solution used is a combination of organic substances and inorganic substances in the shellfish of the organism, and it is more effective than the compatibility of the ions alone.

The FIGURE shows the test results of each ion content in the calcium-based ion solution obtained by pearl extraction.

The nature and flavor classification of shell: (excerpted from the *Compendium of Materia Medica*, [indications] see related text).

(1) Oyster shell: [Nature and flavor] salty, mild, slightly cold, non-toxic. *Fritillaria* is in concerted application with liquorice root, native achyranthes, milkwort root, common cnidium fruit, ephedra, biond magnolia flower-bud, medicinal evodia fruit, chimney sand solution.

(2) Clam shell: [Nature and flavor] salty, cold, non-toxic.
(3) Pearl: [Nature and flavor] salty, sweet, cold, non-toxic.
(4) Abalone shell: [Nature and flavor] salty, mild, non-toxic.
(5) Sea clam: [Nature and flavor] bitter, salty, mild, non-toxic.
(6) Meretrix meretrix linnaeus: [Nature and flavor] salty, mild, non-toxic.
(7) Clam: [Nature and flavor] salty, cold, non-toxic.
(8) Big clam: [Nature and flavor] sweet, salty, mild, non-toxic.
(9) Giant clam: [Nature and flavor] sweet, salty, strong cold, non-toxic.
(10) Cowrie shell [Nature and flavor] salty, mild, toxic.
(11) Purple shell: [Nature and flavor] salty, mild, non-toxic.
(12) Snail: [Nature and flavor] sweet, mild, non-toxic.
(13) Siput: [Nature and flavor] sweet, cold, non-toxic.
(14) Shrimp: [Nature and flavor] sweet, warm, and lightly toxic.
(15) Crab: [Nature and flavor] salty, cold, and lightly toxic.

(VI) Clinical examples of meridian administration:

I. Hyperglycemia:

1. Symptoms: hyperglycemia, spleen deficiency, spleen dampness, and kidney-yin deficiency, accompanied by high cholesterol, constipation and other symptoms.

2. Prescription: atractylodes rhizome 75 g, figwort root 150 g.

3. Proportion of soaking solution: Chinese baijiu 750 ml calcium-based ion solution (crab shell) 55 ml.

4. Soaking time: 25 days. Put it in a spray bottle for use after filtration. Name of this product: hypoglycemic care solution.

5. Applying acupoints: liver meridian, Zhangmen acpoint, spleen meridian, Sanyinjiao acupoint. Twice a day, about 2 ml each time. Spray on the left and right acupoints separately, and massage for 3 minutes at the acupoints to help absorption.

6. Description: Female, 60 years old, with a family history of hyperglycemia and suffering from hyperglycemia for 5 years. She has been oral-taking hypoglycemic for a long time, but the blood glucose index is still high and fasting blood glucose is 7.65. After using "hypoglycemic care solution" for 90 days, the blood glucose decreased from 7.65 to 5.95. Continue oral-taking medicine. With this method, the hypoglycemic effect was obvious.

II. Hyperlipidemia:

1. Symptoms: Hyperlipidemia. Headache, dizziness, stretching, numbness of fingers, hot and oppression in chest, dry stool.

2. Prescription: honeysuckle bud and flower 36 g, weeping forsythia capsule 30 g, chrysanthemum flower 36 g, cassia tora 45 g.

Lotus leaf 36 g, alisma 36 g, tuckahoe 30 g, honeysuckle stem 45 g.

3. Proportion of soaking solution: Chinese baijiu 2,000 ml calcium-based ion solution (crab shell) 150 ml.

4. Soaking time: 30 days. Put it in a spray bottle for use after filtration. Name of this product: hypolipidemic care solution.

5. Applying acupoints: pericardium meridian, Quze acpoint. Liver meridian and liver, Sanyinjiao acupoint. Twice a day, about 2 ml each time.

6. Description: Female, 62 years old, with high blood lipid and a total cholesterol of 6.75%. After using "hypolipidemic care solution" for 45 days, blood lipid was controlled at 3.2% without recurrence.

III. Prostatic Hyperplasia:

1. Symptoms: kidney deficiency, cold and heat, constipation with abdominal pain, subcostal pain, bradyuria, urinary urgency, urinary frequency at night and other symptoms.

2. Prescription: rhubarb root and rhizome 35 g, giant typhonium rhizome 40 g, motherwort herb 90 g 3. Proportion of soaking solution: Chinese baijiu 700 ml calcium-based ion solution (oyster shell) 50 ml.

4. Soaking time; 15-20 days. Put it in a spray bottle for use after filtration. Name of this product: prostate care solution.

5. Applying acupoints: Shimen acupoint of Ren meridian. Two times a day, about 1.5 ml each time. Massage at the acpoint and abdomen for three minutes after administration.

6. Description: Male, 70 years old, suffering from prostatic hyperplasia for ten years. The effect of oral-taking medicine was not obvious, but after using the "prostate care solution" for two weeks, the urine flow increased and the urinary frequency was improved. After continuous use of the prostate care solution for 90 days, the symptoms were significantly improved and did not recur after discontinuation.

IV. Urinary Tract Infection:

1. Symptoms: fever, aversion to cold, abdominal pain, bradyuria, urinary urgency, urinary frequency. Astringent urine, burning pain of urinary tract.

2. Prescription: milkvetch root, debark peony root, kudzuvine root powder of 20 g each, liriope root tuber, coastal glehnia root, chrysanthemum flower of 15 g each, smoked plum, thunberbg fritillary bulb, lophatherum herb, starwort root of 10 g each, millet sprout 30 g.

3. Proportion of soaking solution: Chinese baijiu 1,500 ml calcium-based ion solution (oyster shell) 150 ml.

4. Soaking time: 15-20 days. Put it in a spray bottle for use after filtration. Name of this product: urinary tract infection care solution.

5. Applying acupoints: bladder meridian, Baliao acupoint. Shimen acupoint of Ren meridian. Two times a day, about 1.5 ml each time.

Massage at the acupoint for three minutes after administration.

6. Description: Female, 58 years old, suffering from urinary frequency and pain of urinary tract.

After using "urinary tract infection care solution" for a week, the symptoms were improved and she recovered after two weeks.

V. Chronic Nephritis (Proteinuria):

1. Symptoms: mild edema, exhaustion, backache, deficient sweating. Urine test: protein (++). 2. Prescription: mantis egg-case, milkwort root, bone fossil of big mammals, grassleaf sweetflag rhizome, ginseng, poria with hostwood, Chinese angelica, tortoise carapace and plastron of 30 g each. *Note: supplement with 10 g white mulberry root-bark. White mulberry root-bark soaked in water in concerted application with mantis egg-case for kidney meridian.

3. Proportion of soaking solution: white wine 2,000 ml calcium-based ion solution (Siput) 150 ml.

4. Soaking time: 30 days. Put it in a spray bottle for use after filtration. Name of this product: proteinuria care solution.

5. Applying acupoints: kidney meridian, Qi acupoint. Two times a day, 2 ml each time.

6. Description: Female, 62 years old, suffering from proteinuria for 6 months, unstable, 4 weeks of using proteinuria care solution, no other discomforts except for mild backache, edema disappeared. Another urine test: protein (−). The effect was obvious.

VI. Uterine Fibroids:

1. Symptoms: started to suffer from backache and abdominal pain without obvious cause 7 years ago and the pain aggravated during menstruation. Gynecological B-mode ultrasound diagnosis: 8.0 cm×5.3 cm×3.6 cm, diagnosed as uterine fibroids.

2. Prescription: cassia twig 36 g, tuckahoe, peony root, common buried rubber, zedoray rhizome, pangolin scales, turtle carapace, raw oyster shell of 45 g each, tree peony root bark 30 g, raw liquorice root 18 g.

3. Proportion of soaking solution: Chinese baijiu 2,500 ml calcium-based ion solution (oyster shell) 200 ml.

4. Soaking time: 30 days. Put it in a spray bottle for use after filtration. Name of this product: uterine fibroids care solution.

5. Applying acupoints: extrachannel acupoint of the abdomen, 3 cuns side release across the central line, 4 cuns (1 can is about 3.33 centimeters) below the umbilical region. Twice a day, about 2 ml each time.

6. Description: Female, 38 years old, suffering from increasing menstrual flow for years and prolonged menstruation, diagnosed as uterine fibroids. After using "uterine fibroids care solution" for 4 months, no fibroids were found after further examination.

VII. Liver Cysts:

1. Symptoms: "Liver pain for a long time leads to accumulation and blockage of phlegm, diagnosed as enlarged liver cyst.

2. Prescription: cassia twig, tree peony root bark, peach seed, pinellia tuber, charred triplet of 30 g each, milkvetch root, tuckahoe, orange fruit, peony root, danshen root of 45 g each, raw coix seed 60 g, raw liquorice root 20 g.

*Note: Charred triplet consists of charred malt, charred hawthorn and charred Shenqu.

3. Proportion of soaking solution: Chinese baijiu 3,000 ml calcium-based ion solution (oyster shell) 300 ml.

4. Soaking time: 25-30 days. Put it in a spray bottle for use after filtration. Name of this product: liver cysts care solution.

5. Applying acupoints: liver meridian, Qimen acupoint, Zhangmen acupoint. Twice a day, about 2 ml each time.

6. Description: Female, 58 years old, suffering from repeated pain in the upper abdomen for 3 years. She has visited many hospitals and oral-taken many traditional Chinese medicine and Western medicine, symptoms alleviate sometimes. In the past three months, the upper abdominal distension aggravated. After using "liver cysts care solution" for 4 months and oral-taking traditional Chinese stasis-removing medicine, the symptoms were improved and the cyst became smaller. The effect was obvious.

VIII. Parkinson's Disease:

1. Symptoms: The hands shake involuntarily and they shake too badly to hold things. The upper limb joints are stiff, movements are slow, words are too slurred to understand, expression is dull. The neurology department's diagnosis is Parkinson's disease.

2. Prescription: fleeceflower root, debark peony root, Chinese angelica, milkvetch root, danshen root, barbary wolfberry fruit, earthworm, kudzuvine root, raw bone fossil of big mammals, raw oyster shell, honeysuckle stem of 75 g each, tortoise shell, turtle carapace of 75 g each, largehead atractylodes rhizome 100 g, wine-treated rhubarb 40 g.

3. Proportion of soaking solution: Chinese baijiu 3,000 ml calcium-based ion solution (big clam) 200 ml.

4. Soaking time: 30-35 days. Put it in a spray bottle for use after filtration. Name of this product: Parkinson care solution.

5. Applying acupoints: Ren meridian, Du meridian, liver meridian, spleen meridian, kidney meridian, gallbladder meridian. Baihui, Zanzhu, Yintang, Temple, Shuaigu, Fengchi, Jianjing, Neiguan, Ganshu, Shenshu, Yanglingquan, Taixi, Tsusanli, Sanyinjiao, Yongquan, Qiaogong acupoints. Two times a day, apply an appropriate quantity each time.

6. Description: Male, 80 years old, suffering from Parkinson's disease for 8 years. Treatment: Dredge Ren meridian and Du meridian, massage liver meridian and spleen meridian, kidney meridian, gallbladder meridian and limbs' meridian along with acupoints for administration. After 6 months of treatment, the effect was obvious.

IX. Neurasthenia:

1. Symptoms: Insomnia, restlessness, chest tightness, shortness of breath and abdominal distension.

2. Prescription: safflower 24 g, costus root 24 g, cortex mori 12 g, areca peel 24 g, calamus 24 g, milkwort root 12 g, Chinese arborvitae kernel 12 g, Chinese angelica 20 g, rhubarb 12 g.

3. Proportion of soaking solution: Chinese baijiu 1,500 ml calcium-based ion stock solution (pearl) 75 ml.

4. Soaking time: 15-20 days. Put it in a spray bottle for use after filtration. Name of this product: neurasthenic care solution.

5. Applying acupoints: extrachannel acupoint, Sishengcong, Dangyang, Temple acupoints. Apply Shenmen acupoint and Sanyinjiao acupoint at the same time. Twice a day, about 2 ml each time.

6. Description: Male, 42 years old, with a 7-year history of insomnia. Moody, insomnia, restlessness, constipation. After using "neurasthenic care solution" for a week, his emotions were improved and he could sleep for 3-4 hours a day. After 30 days, he slept better with stable emotions.

X. Cardiovascular Disease (Cerebral Arteriosclerosis):

1. Symptoms: dizziness, numbness of hands, weakness of legs, occasional palpitation, excessive sweating, anorexia, poor defecation. Diagnosed by the neurology department: arteriosclerosis, cerebral ischemia.

2. Prescription: Chinese angelica, unprocessed rehmannia root, Safflower, achyranthes of 18 g each, peach seed 24 g, platycodon root, Szechuan lovage rhizome of 9 g each, peony root, orange fruit of 12 g each, Chinese thorowax root, liquorice root of 6 g each.

3. Proportion of soaking solution: Chinese baijiu 700 ml calcium-based ion solution (oyster shell) 50 ml.

4. Soaking time: 30 days. Put it in a spray bottle for use after filtration. Name of this product: arteriosclerosis care solution.

5. Applying acupoints: pericardium meridian, Quze acpoint. Two times a day, 2 ml each time, and pat 100 times each.

6. Description: Male, 82 years old, after using "arteriosclerosis care solution" for 45 days, dizziness and numbness of hands were alleviated, appetite was improved, excessive sweating was stopped. The effective was obvious.

XI. Trigeminal Neuralgia:

1. Symptoms: facial trigeminal neuralgia, paroxysmal, knife-cut-like pain breaks out once a day. It often flared up and stopped suddenly. Each time lasts 2-3 minutes. Diagnosed as: the first branch trigeminal neuralgia on the left side.

2. Prescription: Szechuan lovage rhizome, dandelion, Chinese violet of 45 g each, acanthopanax 15 g, scorpion, Chinese angelica, dahurian angelica root, herba aristolochiae mollissimae, tortoise-shell glue of 30 g each, camphor, manchurian wildginger of 10 g each.

3. Proportion of soaking solution: Chinese baijiu 1,500 ml, calcium-based ion solution (crab shell) 120 ml.

4. Soaking time: 30 days. Put it in a spray bottle for use after filtration. Name of this product: trigeminal neuralgia care solution.

5. Applying acupoints: Ashi meridian (spray the painful area). Twice a day, about 1-2 ml each time.

6. Description: Female, 65 years old, suffering from the pain of head and face on the left side for 5 years, and no improvement after the treatment of traditional Chinese medicine, Western medicine and acupuncture. After spraying "trigeminal neuralgia care solution" to the painful area, the pain symptoms were alleviated immediately and automatically, 15 days later, and the symptoms disappeared. The effective was obvious.

XII. Eye Disorders:

1. Symptoms: red eyes, distension pain, blurred vision, fear of light, easy to shed tears. It is a virtual fire and excess-heat syndrome.

2. Prescription: (grinding powder) Dandelion 100 g, achyranthes 50 g.

3. Proportion of soaking solution: Chinese baijiu 700 ml calcium-based ion solution (pearl) 20 ml.

4. Soaking time: 30 days. Put it in a spray bottle for use after filtration. Name of this product: eye care solution.

5. Applying acupoints: extrachannel acupoint of the head and neck, Yiming acupoint, Sizhu acupoint (around the tip of the brow), massage for three minutes. Apply the solution to the upper and lower eyelids and gently massage for two minutes.

*Note: The solution has an irritation and cannot enter the eye directly.

6. Description: Male, 62 years old. After a long time of eye work, there will be blurred vision and swollen eyes and so on. The symptoms were improved significantly after using "eye care solution". Daily use can remove the blurred vision and benefit your eyes.

Fill the preparation extracted from the solution in a pressure-free spray bottle for use. The administration is simple, convenient and easy to carry. A bottle of 30 ml of the solution can be used for a course, about 15 days. The administration can be completed in 2-3 minutes per use.

The above descriptions are only the preferred schemes of the invention, and it should be noted that for ordinary technicians in the technical field, without departing from the principles of the invention, some improvements and polishing can also be made, and these improvements and polishing should also be considered as the scope of protection of the invention.

The invention claimed is:

1. A method for processing traditional Chinese medicine using calcium-based ion solution, wherein ingredients of the traditional Chinese medicine are soaked in a solution composed of a calcium-based ion solution and Chinese baijiu, and the calcium-based ion solution is a solution with a mass percentage concentration of calcium ion of 0.3%-10%, and the Chinese baijiu is at 35-75% alcohol by volume.

2. The method for processing traditional Chinese medicine using calcium-based ion solution according to claim 1, wherein the calcium-based ion solution is obtained by soaking shells in a dilute hydrochloric acid solution, and the shells are one or more of oyster shell, clam shell, pearl, abalone shell, sea clam, clam, big clam, giant clam, purple shell, snail, siput, shrimp shell and crab shell.

3. The method for processing traditional Chinese medicine using calcium-based ion solution according to claim 1, wherein the traditional Chinese medicine is for treating freckles, eye bags, skin whitening, hair tonic, dandruff shampoo, gout, vitiligo, eczema, psoriasis, itchy skin, arthritis and degenerative diseases, foot dampness dispelling, athlete's foot, foot dredge meridians, female mammary hyperplasia, stretch marks, prostatitis, skin cancer, hyperglycemia, hyperlipidemia, prostatic hyperplasia, urinary tract infection, chronic nephritis, proteinuria, uterine fibroids, lung nodules, liver cysts, gallstones, fatty liver, neurasthenia, tumors, cervical spondylosis, pain in neck shoulder low-back and leg, muscle cramp, frozen shoulder, sports muscle injury, male sexual function, Parkinson's disease, cardiovascular diseases, trigeminal neuralgia, mastitis, neuropathic pain, Alzheimer's disease, eye disorders and for treating diseases related to wormwood extract.

4. An administration route of traditional Chinese medicine prescription obtained by the method for processing traditional Chinese medicine using calcium-based ion solution of claim 1, which is a transdermal and meridians therapy.

5. A soaking solution for processing a traditional Chinese medicine, wherein the soaking solution is a solution composed of a calcium-based ion solution and Chinese baijiu, and the calcium-based ion solution is a solution with a mass percentage concentration of calcium ion of 0.3%-10%, and the Chinese baijiu is at 35-75% alcohol by volume.

6. The soaking solution for processing the traditional Chinese medicine according to claim 5, wherein the calcium-based ion solution is obtained by soaking shells in a dilute hydrochloric acid solution, and the shells are one or more of oyster shell, clam shell, pearl, abalone shell, sea clam, clam, big clam, giant clam, purple shell, snail, siput, shrimp shell and crab shell.

7. A method for making a transdermal administration coating agent of traditional Chinese medicine prescription, comprising soaking the traditional Chinese medicine prescription in the soaking liquid for processing traditional Chinese medicine as claimed in claim 5.

8. The method according to claim 7, wherein the traditional Chinese medicine is for treating hyperglycemia, hyperlipidemia, prostatic hyperplasia, urinary tract infection, chronic nephritis, proteinuria, uterine fibroids, lung nodules, liver cysts, gallstones, fatty liver, neurasthenia, tumors, cervical spondylosis, pain of neck, shoulder, low-back and leg, muscle cramp, frozen shoulder, sports muscle injury, male sexual function, Parkinson's disease, cardiovascular diseases, trigeminal neuralgia, mastitis, neuropathic pain, Alzheimer's disease, eye disorders and for treating diseases related to wormwood extract.

* * * * *